(12) United States Patent
Taub et al.

(10) Patent No.: US 6,414,114 B2
(45) Date of Patent: Jul. 2, 2002

(54) DISULFIDES AND THIOL COMPOUNDS

(75) Inventors: Floyd E. Taub, Silver Spring, MD (US); Christopher K. Murray; Randall J. Daughenbaugh, both of Boulder, CO (US); Daniel Lednicer, North Bethesda, MD (US)

(73) Assignee: Dovetail Technologies, Inc., College Park, MD (US)

( * ) Notice: Subject to any disclaimer, the term of this patent is extended or adjusted under 35 U.S.C. 154(b) by 0 days.

(21) Appl. No.: 09/256,765

(22) Filed: Feb. 24, 1999

Related U.S. Application Data

(60) Provisional application No. 60/085,474, filed on May 14, 1998, and provisional application No. 60/075,966, filed on Feb. 24, 1998.

(51) Int. Cl.$^7$ ............................. C07K 5/00; C07K 4/00
(52) U.S. Cl. ................ 530/330; 530/326; 530/327; 530/328; 530/329; 530/331; 530/332; 930/20; 930/260
(58) Field of Search ............... 530/320–332; 930/20, 260

(56) References Cited

U.S. PATENT DOCUMENTS

| | | | |
|---|---|---|---|
| 3,789,125 A | 1/1974 | Kuger et al. | 424/324 |
| 4,102,948 A | 7/1978 | Feuer et al. | 260/944 |
| 4,499,080 A | 2/1985 | Duflot et al. | 514/12 |
| 5,102,871 A * | 4/1992 | Furukawa et al. | 514/11 |
| 5,223,488 A | 6/1993 | Ogata et al. | 514/18 |
| 5,578,313 A | 11/1996 | Knight et al. | 424/423 |
| 5,643,966 A | 7/1997 | Knight et al. | 514/626 |
| 5,679,643 A | 10/1997 | Kauvar et al. | 514/18 |

FOREIGN PATENT DOCUMENTS

| | | |
|---|---|---|
| WO | WO 97/14306 | 4/1997 |

OTHER PUBLICATIONS

Knight, G.D. et al. Seemingly Diverse Activities of B–Alethine. Cancer Research. Nov. 1, 1994. vol. 54, pp. 5636–5642, see especially Abstract, Fig. 1 and pp. 5636–5637.

Oiry, J. et al. Synthesis and Radioprotective Activity of New Cysteamine and Cystamine Derivatives. J. Med. Chem. Nov. 1986, vol. 29, No. 11, pp. 2217–2225, see especially Abstract and pp. 2218–2219.

* cited by examiner

Primary Examiner—Bennett Celsa
(74) Attorney, Agent, or Firm—Judith A. Evans

(57) ABSTRACT

The present invention is directed to novel disulfides and thiols that are of up to about eighteen amino acids. One example, is a compound of the formula (1): A—B—C—S—S—D—E—F, wherein: A and F are selected from the group consisting of hydrogen, an amino acid, a dipeptide, a tripeptide, a modified polypeptide up to three amino acids long, and a carbobenzoxy groups, B and E are selected from the group consisting of an amino acid, a dipeptide, a tripeptide, and a modified polypeptide comprising up to and including three amino acids, C and D are selected from the group consisting of a modified polypeptide and a polypeptide comprising up to and including three amino acids, and S is the sulfur atom in the modified polypeptide and the polypeptide in C and D.

3 Claims, No Drawings

DISULFIDES AND THIOL COMPOUNDS

This application claims priority to U.S. Provisional Application No. 60/075,966, filed Feb. 24, 1998 and No. 60/085,474, filed May 14, 1998 which are incorporated herein in their entirety.

FIELD OF THE INVENTION

This invention relates to novel disulfides and thiols of up to about eighteen amino acids.

BACKGROUND

The predominant small molecule disulfide in the cell is glutathione. The majority of intracellular glutathione is present in its reduced thiol form, which contributes to intracellular reducing conditions. The intermolecular disulfide in glutathione is far less stable than intramolecular protein disulfides and can rapidly convert between thiol and disulfide. Creighton, T. E., *Proteins.* New York, N.Y. W. H. Freeman & Co., 1993. Other similar disulfides, are also likely to affect the redox equilibrium. Cellular thiols/disulfides are thought to be important in determination of protein structure by enabling the formation of disulfide bonds between Cys residues via thiol-disulfide exchange. Protein-bound free SH— groups also play key roles in regulating DNA transcription and binding of regulatory proteins to DNA. A variety of metabolic pathways are significantly impacted by redox state, since thiols have been shown to control the activity of numerous enzymes. Gilbert, H. F., Adv. Enzymol. Metab. Relat. Areas 63:69, 1990; Ziegler, D. M., Ann. Rev. Biochem. 54:305, 1985. Regulation of enzyme systems may play a critical role in maintaining cellular homeostasis and preventing oxidative stress. Reactive oxygen intermediates such as peroxides also have regulatory effects. Therefore, there is a need for new disulfide and thiol molecules that can be potentially useful as agents that affect oxidation-reduction equilibrium in a cell.

SUMMARY OF THE INVENTION

It is an object of the present invention to provide novel disulfides and thiols that are small molecules. In one aspect, the compound is of the formula (1): A—B—C—S—S—D—E—F, wherein: A and F are selected from the group consisting of hydrogen, an amino acid, a dipeptide, a tripeptide, a modified polypeptide up to three amino acids long, and a carbobenzoxy group, B and E are selected from the group consisting of an amino acid, a dipeptide, a tripeptide, and a modified polypeptide comprising up to and including three amino acids, C and D are selected from the group consisting of a modified polypeptide and a polypeptide comprising up to and including three amino acids, and S is the sulfur atom in the modified polypeptide and the polypeptide in C and D.

In another aspect, the compound is of the formula (II): A—B—C—S, wherein: A is selected from the group consisting of hydrogen, an amino acid, a dipeptide, a tripeptide, a modified polypeptide up to three amino acids long, and a carbobenzoxy group, B is selected from the group consisting of an amino acid, a dipeptide, a tripeptide, and a modified polypeptide comprising up to and including three amino acids, C is selected from the group consisting of a modified polypeptide and a polypeptide comprising up to and including three amino acids, and S is the sulfur atom in the modified polypeptide and the polypeptide in C.

DETAILED DESCRIPTION OF THE INVENTION

In a first embodiment, the present invention relates to novel disulfide and thiol compounds of the Formula I:

A—B—C—S—S—D—E—F

Wherein:
A and F independently may be hydrogen, an amino acid, a di- or tri-peptide, a modified polypeptide up to 3 amino acids long, a carbobenzoxy or other ring structure known in the art to facilitate lipid solubility and/or provide other beneficial pharmacologic properties. Hydrophobic amino acids, aromatic amino acids including tryptophan, and phenylalanine, are especially preferred.

B and E independently may be an amino acid, a di or tri-peptide, or a modified polypeptide up to 3 amino acids long. In a preferred embodiment, B and/or E are neutral amino acids.

C and D independently may be a modified polypeptide or traditional polypeptides up to 3 amino acids long. In a preferred embodiment, C and/or D are neutral amino acids.

S denotes the sulfur in the amino acids in C and D.

In a preferred embodiment A, B, C, D, E, F are single amino acids or in some cases a dipeptide. Hydrophobic or hydrophilic amino acids, may be used to alter biodistribution and bioactivity.

The identity of A and F and of each of the lettered moieties in the other pairs may be distinct from the other member of the pair and also from any moiety in any of the pairs. Thus, the molecules may be homo- or heterodimers.

Specific examples of half molecules, which may be combined in a fashion to form dimers include but are not limited to:

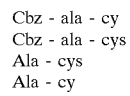

Cbz - ala - cy
Cbz - ala - cys
Ala - cys
Ala - cy

Key:
ala—alanine (preferably beta-alanine)
cys—cysteine
cy—cysteamine

In the most preferred embodiment, the beta form of alanine is used in the above examples or as A or B or E or F. D and L forms of all amino acids are also within the scope of this invention.

Any ring structure may be substituted for the Cbz group using any of a variety of linkages known to those skilled in the art. Any relatively neutral amino acid may be substituted for ala; these include b-alanine, valine, leucine, isoleucine, proline, phenylalanine, tryptophan, methionine, glycine, serine, threonine, cysteine, tyrosine, aspergine, glutamine (to include both D and L forms of these compounds). Any other thiol-containing molecule or other molecule capable of dimerizing may be substituted for cysteine. The present invention includes the half molecules diagramed above and modified half molecules which have an attached phosphate group (—PO3H2) or other similar group. It also includes, but is not limited to phosphate (—OPO$_3$H$_2$), phosphorus acid (—PO$_3$H$_3$), hydrogen sulfate (—OSO$_3$H) sulfonic acid (—SO$_3$H), sulfinic acid (—SO$_2$H), sulfenic acid (—SOH), and metallic salts of these species. In a preferred embodiment, the attached phosphate group or similar group may be removed from the half molecule under physiologic conditions.

In the most preferred embodiment, beta-alanine is used in A, B, C, D, E, and/or F. The following compounds are representative of the novel disulfides and thiols of the present invention:

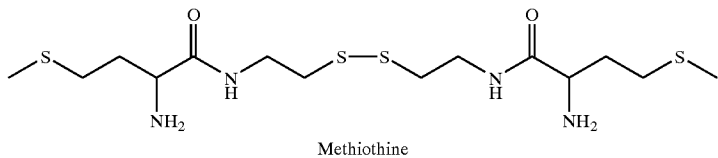
Methiothine
And corresponding monomer;
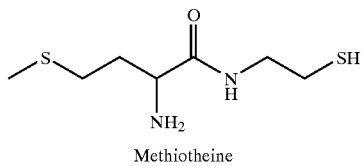
Methiotheine
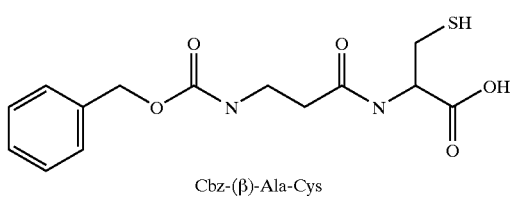
Cbz-(β)-Ala-Cys
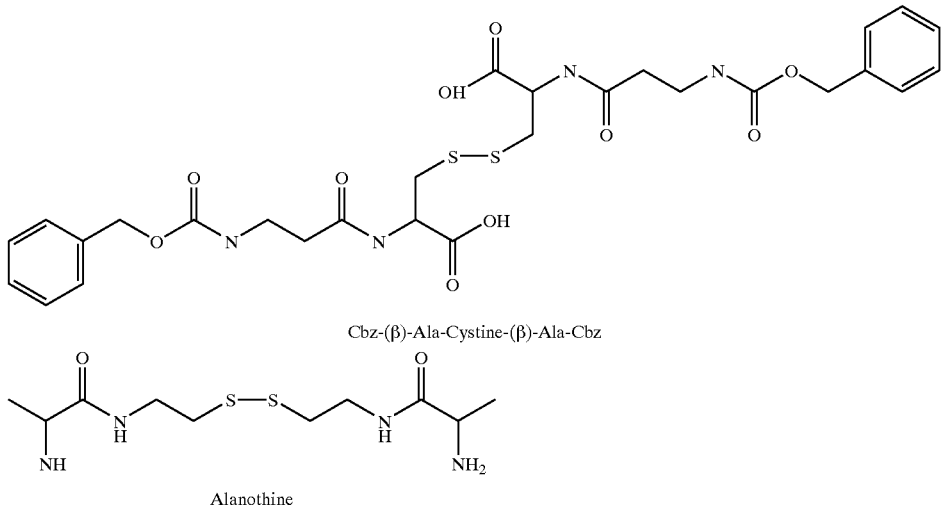
Cbz-(β)-Ala-Cystine-(β)-Ala-Cbz
Alanothine
And corresponding monomers;
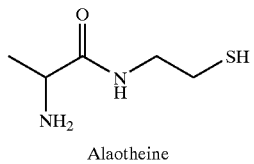
Alaotheine
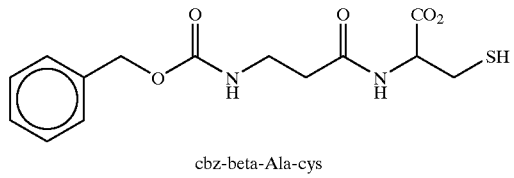
cbz-beta-Ala-cys
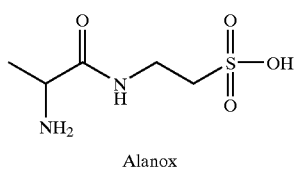
Alanox
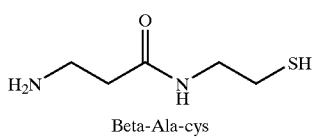
Beta-Ala-cys

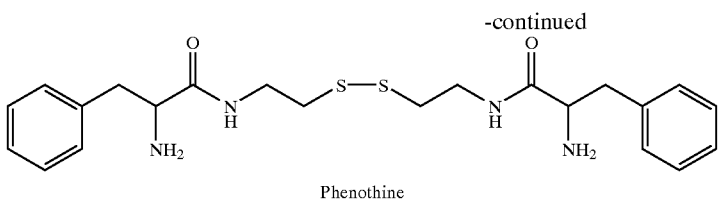
Phenothine

And corresponding monomers;

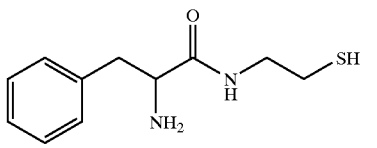
Phenotheine

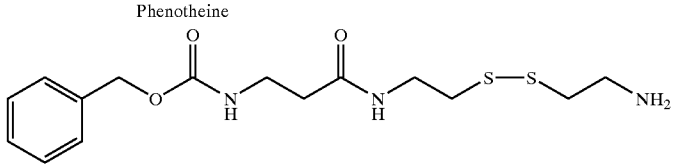
Compound A

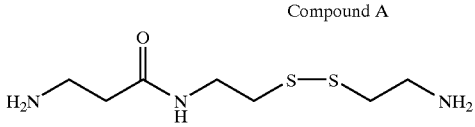
Compound B

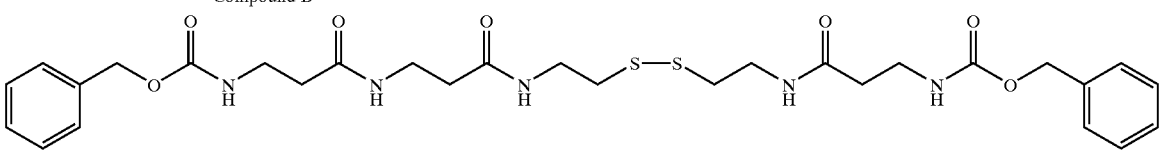
Compound C

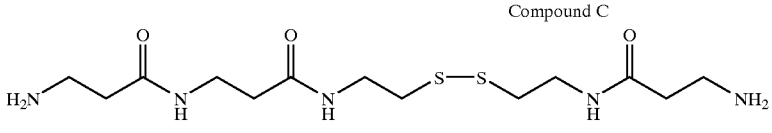
Compound D

All of the compounds of the present invention can be synthesized using routine methods known to those skilled in the art without undue experimentation. Indeed many companies now exist that routinely make small molecules such as those of the present invention on a made-to-order basis based on the structure of the compound alone. The Examples set forth below provide protocols for making certain compounds that are representative compounds of the present invention. Simple variations on the protocols set forth in the Examples can be determined to make other compounds of the present invention by persons skilled in the art.

Beta-alanyl cysteamine disulfide (Betathine™, Beta LT™, BT, also beta-alethine) is a dimer composed of two small thiols which has diverse biological activity. Recently β-alethine has been shown to exhibit potent antitumor activity in vivo. For example, in an NS-1 mouse myeloma model, repeated administration of β-alethine as a monotherapy soon after inoculation with relatively low doses of tumor significantly increased survival rates. Treatment with β-alethine was also found to increase the percent survival in the Cloudman S-91-DBA/2 model in which melanomas had already been established. U.S. Pat. No. 5,643,966; U.S. Ser. Nos. 08/468,043; 08/468,041; 08/346,177. β-alethine has been used as an adjunct to chemotherapy in two aggressive murine tumor models, where it was admin along with melphalan in the treatment of the MOPC-315 myeloma and with cyclophosphamide in the treatment of the B16 melanoma, and it was found to be a beneficial adjunct to chemotherapy in both systems. U.S. Provisional Application Nos. 60/075,966 and 60/085,474, which are incorporated herein in their entirety. Despite the growing body of in vivo studies showing the antineosplastic effects of BT, the underlying mechanism had not been determined.

Beta-alethine and certain other thiols and disulfides (described in U.S. Ser. No. 08/733,174) have also been used as adjuvants in vaccines and as immunostimulatory molecules. Further, the compounds beta-alanyl taurine and carbobenzoxy beta-alanyl taurine and related compounds collectively called Taurox™ have been used as anti-cancer agents (U.S. Pat. Nos. 5,370,818; 5,578,313), for the therapeutic treatment of immune diseases (U.S. Ser. Nos. 08/466,143; 08/469,697); and in cell culture and therapy (U.S. Ser. Nos. 08/463,732 and 08/463,784). All of the above patents and applications are incorporated by reference into this application in their entirety.

Without meaning to be bound by theory, the structure of β-alethine suggests that its disulfide moiety may be crucial for activity. The predominant small molecule disulfide in the cell is glutathione. The majority of intracellular glutathione is present in its reduced thiol form, which contributes to intracellular reducing conditions. The intermolecular disulfide in glutathione is far less stable than the typical intramolecular protein disulfides and can rapidly convert between the thiol and disulfide forms. Other similar disulfides, such as BT, and their corresponding thiols, are also likely to affect the redox equilibrium. Cellular thiols/disulfides are thought to play an important role in determining protein structure by enabling the formation of disulfide bonds between Cys residues via a thiol-disulfide exchange. A variety of metabolic pathways are also known to be significantly impacted by redox state, and thiols have been shown to control the activity of numerous enzymes Various aspects of the present invention are described in greater detail in the non-limiting Examples that follow.

EXAMPLES

Example I

Cbz-beta-Ala-Cystine-beta-Ala-Cbz

The compound Cbz-betaAla-Cystine-betaAla-Cbz was synthesized using the following protocol:

Step 1. A first solution was prepared by dissolving 1 mmol of cystine in 20 ml of a 5% $NaHCO_3/H_2O$ solution. The solution was then cooled to 0 degrees centigrade.

Step 2. A second solution was prepared by dissolving 2.5 mmol of Cbz-beta-Ala and 2.6 mmol of N-Hydroxysuccinimide in 20 ml of acetonitrile and cooled to −15 degrees centigrade. 2.6 mmol of dicycolhexylcarbodiimide (DCC) were then added to the cool solution. The solution was removed from the cold bath and the reaction was allowed to proceed at room temperature for 1 hour.

Step 3. Precipitates were filtered off of the solution of step 2 after the reaction was complete, and the filtrate was then cooled to −15 degrees centigrade. The cystine solution of step 1 was mixed with the filtrate at 0 degrees. The mixture was then stirred at −15 degrees centigrade for 10 min followed by another 1 hour stirring at room temperature.

Step 4. The reaction mixture from step 3 was acidified with aqueous HCl followed by extraction with dichloromethane.

Step 5. The organic layer of the extract of step 4 was dried over $MgSO_4$, filtered and the dichloromethane allowed to evaporate. Step 6. The dried product from step 5, the disulfide Cbz-beta-Ala-Cystine-beta-Ala-Cbz, was then purified by HPLC and analyzed by mass spectroscopy.

Methods (such as catalytic hydrogenation) known to persons of skill in the art can be used to remove the Cbz protecting groups to make beta-Ala-Cystine-Beta-Ala, or the reduced thiol form.

| Sequence | Cbz-βAla-Cystine-βAla-Cbz |
|---|---|
| HPLC Analysis. | |
| Instrument: | Shimadzu |
| HPLC File ID: | c:\class-vp\chrom\wall-2 |
| Flow Rate: | 0.4 ml/min |

-continued

| Sequence | Cbz-βAla-Cystine-βAla-Cbz |
|---|---|
| Gradient: | 10%–90% B in 15 min; A: 0.1% TFA/water, B: 0.1% TFA/acetonitrile |
| Column: | HIASIL ™, C18, 5 micron |
| Ret. Time: | 10.58 min |
| Detection: | 220, 240, 256, 278 |
| Purity: | >95% |
| IonSpray MS Analysis. | |
| Instrument: | Perkin Elmer, Sciex APII |
| Data File ID: | Wallace-2/Scans 103–133 |
| State File ID: | ppg pos |
| Method: | FLA |
| MS Expected: | 650.7 |
| MS Found: | 651.4 |

Solubility: Soluble in 30% Acetonitrile/water.

Example II

Cbz-beta-Ala-Cys

Cbz-beta-Ala-Cys was prepared using the following procedure:

Step 1. 0.5 mmol of Fmoc-Cys(trt)-(2-Chlorotrityl Resin) was washed with Dimethylformamide (DMF) three times in a glass reaction vessel. The Fmoc was then removed by treating with 20% piperidine in DMF for 30 min.

Step 2. The solution from step one was washed with DMF five times to remove the piperidine.

Step 3. Dissolve 2 mmol of Cbz-beta-Ala, 2 mmol of o-benzotriazol-1yl-N,N,N',N'-tetramethyluronium hexaflurophosphate (HBTU) and 2 mmol of HOBT in 4 ml of DMF.

Step 4. Add the mixture from step 3 to the piperidine-treated resin, then add 2 mmol of N,N-diisopropylethylamine (DIEA). Swirl the mixture for 1 hour at room temperature.

Step 5. Wash the peptide-resin with DMF (5 times) and with dichloromethane (3 times).

Step 6. Cleave the peptide by treating for 1 hour with 10 ml trifluroacetic acid (TFA) plus 0.5 ml triethylsilane.

Step 7. Filter and evaporate the TFA to obtain Cbz-beta-Ala-cys, then analyzed by HPLC and Mass spec.

Step 8. Purify the Cbz-Beta-Ala-cys product using HPLC and analyze using mass spectroscopy.

Variations on this protocol can by made by those skilled in the art using routine experimentation to make other thiols of the present invention.

| Sequence: | Cbz-beta-Ala-Cys |
|---|---|
| HPLC Analysis. | |
| Instrument: | Shimadzu |
| HPLC File ID: | c:\class-vp\chrom\wall-1 |
| Flow Rate: | 0.4 ml/min |
| Gradient: | 10%–90% B in 15 min; A: 0.1%/TFA/water, B: 0.1% TFA/acetonitrile |
| Column: | HIASIL ™, C18, 5 micron |
| Ret. Time: | 10.84 min |
| Detection: | 220, 240, 256, 278 |
| Purity: | >95% |
| Ionspray | MS Analysis. |

| | |
|---|---|
| Sequence: | Cbz-beta-Ala-Cys |
| Instrument: | Perkin Ehner, Sciex APII |
| Data File ID: | W@-1/Scans 78–80 |
| State File ID: | ppg pos |
| Method: | FIA |
| MS Expected: | 326.4 |
| MS Found: | 327.2 (M + H) |
| Solubility: | Soluble in 20% Acetonitrile/Water |

Example III

Method of Synthesizing β-alethine

The following protocol for synthesizing β-alethine can be adapted by persons of ordinary skill in the art to make the disulfides of the present invention with only routine experimentation. Other protocols for making β-alethine are available in the art.

This protocol consists of 3 synthetic steps and 2 purification steps. Below is a brief description of each step.

Step 1 is the formation of the activated ester from N-Cbz-β-alanine (compound 1). The N-Cbz-/β-alanine activated ester (compound 2) is not isolated instead it is taken directly to step 2 in solution.

Step 2 is the coupling of the activated ester (from step 1) to cystamine dihydrochloride. The product compound is N,N'-bis-Cbz-β-alethine (Compound 3).

Step 3 is the removal of the Cbz groups from N,N'-bis-Cbz-β-alethine using hydrogen bromide (HBr)/acetic acid (AcOH). The resulting compound is β-alethine TM-2HBr (β-alethine hydrobromide salt) (compound 4).

Step 4 uses ion-exchange chromatography to exchange the Br ion on β-alethine-2HBr for a Cl ion and to remove non-ionic organic impurities. The resulting compound is β-alethine (compound 5)

Step 5 is a precipitation of the β-alethine using acetone and water. The resulting compound is the purified final product (compound 5).

Detailed Description of the process

Step 1

N-Cbz-/β-alanine (Compound 1) (P/N 0665 is slurried in anhydrous dichloromethane (P/N 0374) to make a 0.3M solution. To the slurry is added 1 molar equivalent N-hydroxysuccinimide (P/N 0696) and 1 molar equivalent dicyclohexylcarbodiimide (DCC, P/N 1267). The mixture is stirred at room temperature for at least 6 hours and no more than 68 hours. The reaction mixture now contains dicyctohexylurea, a bi product of the reaction, and is a mixture of solids and liquid.

Step 2

The crude mixture is filtered under an argon blanket using a sintered glass funnel. The liquid is filtered into a reaction vessel containing 0.4 molar equivalents of the cystamine dihydrochloride (P/N 0821). The solid dicyclohexylurea (DCU) is washed with 3×200 mL portions of anhydrous dichloromethane. Triethylamine (P/N 0247), 0.8 molar equivalents, is added and the reaction mixture is allowed to stir for at least 12 but no more than 68 hours. The reaction is now a mixture of liquid and solids.

To this crude mixture is added enough HPLC grade acetone (P/N 0828) to equal the amount of dichloromethane present. The mixture is then stirred for 2 to 4 hours before being filtered through a Buchner funnel fitted with Whatman's #541 filter paper (P/N 0286). The solid N,N'-bis-Cbz-β-alethine (Compound 3) (P/N 1277) is then washed with 3,200 mL of HPLC grade acetone. The solid is collected and dried in a vacuum oven at 40° C.

The crude solid, N,N'-bis-Cbz-β-alethine, is slurried in acetonitrile (P/N 2017) to make a 0.3M solution. The mixture is heated to 50° C. to dissolve the solids. Once the solids have dissolved, deionized water (P/N 1793) in an amount sufficient to make 0.15M, is slowly added and the mixture is allowed to cool to room temperature. The purified N,N'-Cbz-β-alethine (P/N 1286) is filtered off using an 18.5 cm Buchner funnel fitted with Whatman's #541 filter paper. The purified solids are washed with deionized water, collected, and dried in a vacuum oven at 40° C.

References: 1) Cancer Research, 1994, 54, 5636–5642. 2) Cancer Research, 1994, 54, 56235635. 3) World Patent WO 92/00955. 4) HCR notebooks 1576-1, 1576-7, 1576-15, 1576-28, 1576-42, 1576-118, 1598-83, 1598-105, 1598-119, 1598-139, 1613-150, 1613-154, 1649-39, 1714-88, 1714-102.

Step 3

The purified N,N'-bis-Cbz-β-alethine is slurried in enough glacial acetic acid (PN 0503) to make a 0.15 M solution. The HBr/AcOH mixture (P/N 1282) is then added and all solids dissolve. The reaction is allowed to stir overnight at room temperature (for at least 15 but no more than 68 hours) during which time the reaction product precipitates out of solution. After mixing enough HPLC grade acetone is added to the reaction mixture to equal one half the amount of glacial acetic acid. The mixture is allowed to mix an additional 2 to 4 hours before being filtered through a Buchner funnel fitted with Whatman's #541 filter paper. The solid β-alethine TM hydrobromide salt (Compound 4) (P/N 1287) is then washed with 3×150 mL volumes of HPLC grade acetone. The solids are collected and dried in a vacuum oven at 40° C.

References: 1) Cancer Research, 1994, 54, 5636–5642. 2) Cancer Research, 1994, 54, 56235635. 3) World Patent WO 92/00955. 4) HCR notebooks 1576-6, 1576-17, 1576-25, 1576-25, 1576-38, 1576-86, 1576-88, 1576-89, 1576-117, 1576-153, 1598-103, 1598-121, 1598-141, 1613-153, 1649-40, 1714-100.

Step 4

A 4"×3' ion exchange column is slurry packed with BioRad Dowex AG 1-X8 chloride form anion-exchange resign (P/N 1408). The slurry solution used is a 1M solution of potassium chloride (KCl) (P/N 1283) in deionized water (P/N 1793). The column is washed with 3 column volumes of the 1M KCl solution followed by 3 column volumes of deionized water. The hydrobromide salt of β-alethine TM (Compound 4) is dissolved in deionized water and filtered through a sintered glass funnel to remove any particulate matter. The filtrate is loaded directly onto the ion exchange column and dispersed. The column is eluted with deionized water and 100 mL fractions are collected. Fractions are spotted on a silica gel plate and tested under a UV lamp. The fractions that contain the product (β-alethine TM) (Compound 5) quench under a UV lamp. Product containing fractions are collected, frozen and lyophilized.

The residual solid is dissolved in 1.5 mL of water for HPLC injection (P/N 0079) per gram of solid. To the aqueous solution is added 10% wt/wt activated carbon (P/N 0472). The slurry is mixed for at least minutes before being filtered. To this solution is added a 10 fold excess of HPLC grade acetone. The mixture is allowed to mix for 1 to 4 hours at room temperature before being filtered through a Buchner funnel fitted with Whatman's #541 filter paper. The solid β-alethine TM is then washed with three, 150 mL of HPLC grade acetone. The solid product is collected and dried in a vacuum oven at 40 degrees centigrade until a constant weight is achieved.

References: 1) Cancer Research, 1994, 54, 5636-5642. 2) Cancer Research, 1994, 54, 56235635. 3) World Patent WO 92/00955. 4), HCR notebooks 1576-6, 1576-17, 1576-25, 1576-25, 1576-38, 1576-86, 1576-88, 1576-89, 1576-117, 1576-153, 1598-103, 1598-121, 1598-141, 1613-153, 1649-40, 1714-100.

Example IV

Beta-alanyl-ethanethiolamine

Beta-alanyl-ethanethiolamine was synthesized by the following procedure:

To a solution containing 2.00 g (5.46 mmol) of betathine (BT) in 50 ml of water was added 0.93 g (6.03 mmol) of dithiothreitol. The reaction was allowed to stir at ambient temperature overnight. HPLC analysis of the reaction mixture indicated approximately 30% starting β-alethine remaining. An additional 0.93 g mixture indicated no starting β-alethine remaining. The solvent was removed under reduced pressure and anhydrous acetonitrile added. The solid was collected by filtration and dried to afford 1.02 g (100%) of product.

$^1$HNMR (D$_2$O) δ2.63–2.70 (m, 4H), 3.25 (t, J=5.9 Hz, 2H), 3.37 (t, J=6.2 Hz, 2H); $^{13}$CNMR (D$_2$O) δ23.39, 32.23, 36.03, 42.40, 172.48; MS Calcd; 148; Found; 149 (M+H)

Example VI

The method set forth below for synthesizing carbobenzoxy or carbobenzoxy beta-alanyl taurine (Taurox™-SB) can be modified by persons skilled in the art to make thiols of the present invention.

A solution containing 49.88 g (223.48 mmol) of carbobenzoxy-beta-alanine (also carbobenzoxy-beta-alanine), 46.11 g (223.48 mmol) of dicyclohexylcarbodiimide and 25.72 g (223.48 mmol) of N-hydroxysuccinimide in 750 ml of dichloromethane was allowed to stir at ambient temperature overnight. The separated N,N'-dicyclohexylurea byproduct was filtered through a glass fritted funnel and the filter cake washed with 250 ml of dichloromethane. The filtrate containing the activated ester is used without further purification.

To the filtrate was added 27.97 g (223.49 mmol) of taurine followed by 34.3 ml (246.09 mmol) of triethylamine. The reaction was allowed stir at ambient temperature for 120 h. The reaction was filtered through a glass fritted funnel and the filtrate concentrated under reduced pressure. The residue was dissolved in water and placed on an ion exchange column (AG 50W-XS, 100–200 mesh, acidic form) conditioned with 1 L of 6N hydrochloric acid and 2 L of water. The product was eluted with de-ionized water and the appropriate fractions combined and the solvent removed under reduced pressure to afford 94.50 g of a viscous oil. Trituration with anhydrous acetonitrile gave 50.94 g (69.00%) of product as a white solid.

$^1$H NMR (DMSO d$_6$) 2.22 (t, J=7.3, 2H), 2.67 (t, J=7.7 Hz, 2H), 3.19 (t, J=6.6 Hz, 2H), 3.32 (bs, 2H), 4.99 (s. 2H), 7.15–7.35 (m. 5H), 7.90 (bs, 1H), 10.13 (s. 1H); $^{13}$C NMR (DMSO d$_6$) 35.40, 35.92, 37.25, 50.65, 65.31, 127.79, 127.87, 128.48, 137.33, 156.15, 170.19, MS Calcd: 330; Found: 329 (M–H)

Variations on the general method set forth in this Example can be used by persons of ordinary skill in the art using routine experimentation to make other thiols of the present invention.

Example VII

The method set forth below for synthesizing carbobenzoxy or carbobenyoxy beta-alanyl taurine (Taurox™-OP) can be modified by persons skilled in the art to make thiols of the present invention.

To a 250 ml Parr flask was added 1.00 g (2.89 mmol) of Taurox BOP in 40 ml of water and 0.2 g of 5% palladium on carbon. The flask was pressurized to 20 psi hydrogen and vented (3×). The flask was then pressurized to 40 psi hydrogen and shaken for 5 h. The flask was vented and the contents filtered through a bed of celite 521 and the filter cake washed with water. The filtrate was concentrated under reduced pressure to afford 490 mg (79.92%) of product.

$^1$H NMR (D$_2$O) 2.69 (t, J=6.6 Hz, 2H), 3.26 (t, J=6.6 Hz, 2H), 3.43 (t, J=5.1 Hz, 2H), 3.91 (ABq, J=5.5 Hz, 2H); $^{13}$C NMR. (D$_2$O) §32.29, 35.92, 40.23(d, J=6.9 Hz), 63.66, 172.48; MS Calcd:: 212; Found: 211 (M–H)

Variations on the method set forth in this Example can be used by persons of ordinary skill in the art using routine experimentation to make other thiols of the present invention.

Example VIII

A synthetic approach such as the following general scheme for making compounds of the present invention can be used as a starting point which can be used by those skilled in the art to make the desired compounds.

Synthetic Approach:

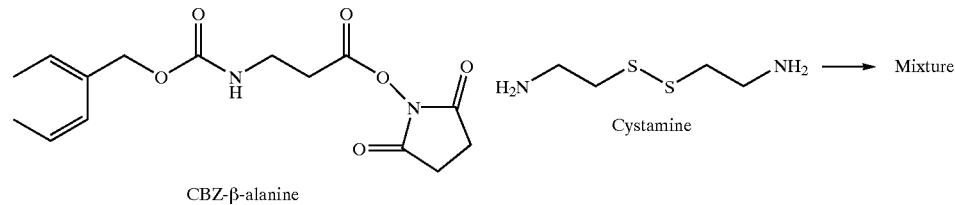

CBZ-β-alanine    Cystamine → Mixture

1:1-2 Mole Ratio

-continued

Separate from mixture the mono addition product:

Take some of the a, above to de-protect

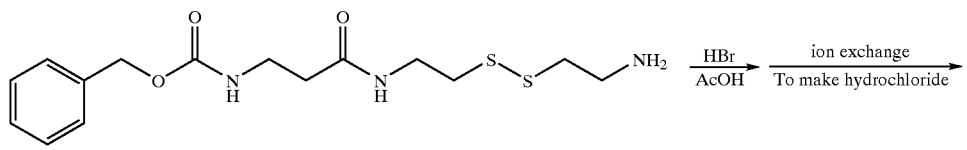

"A"

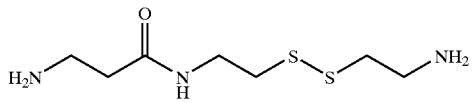

NMR
MP
IR

"B"

Characterize

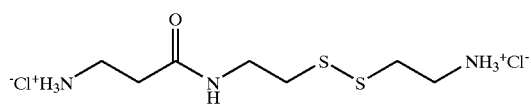

"B as dihydrochloride"

Take B and react with excess CBZ-β-alanine:

Take some of C above and de-protect:

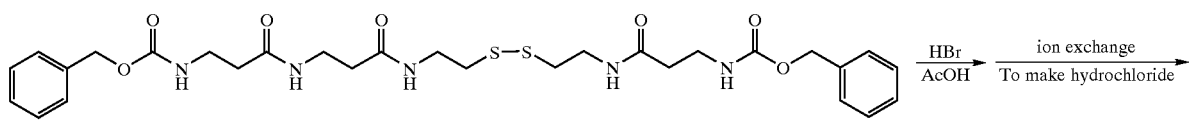

"C"
Characterize

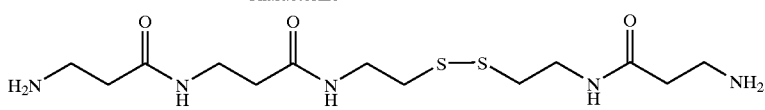

"D"

All documents cited above are hereby incorporated in their entirety by reference. The entire contents of U.S. Provisional Appln. No. 60/005,336, filed Oct. 17, 1995; and No. 60/075,966 and No. 60/085,474, are also incorporated herein in their entirety.

One skilled in the art will appreciate from a reading of this disclosure that various changes in form and detail can be made without departing from the true scope of the invention.

What is claimed is:

1. A compound of formula (1):

A—B—C—S—S—D—E—F wherein:
A and F are selected from the group consisting of hydrogen, an amino acid, a dipeptide, and a carbobenzoxy group;
B and E are selected from the group consisting of amino acid and a dipeptide;
C is cysteamine;
D is an amino acid; and
S is a sulfur atom in the cysteamine in C and in the amino acid in D.

2. A compound of formula (1):

A—B—C—S—S—D—E—F wherein:
A and F are selected from the group consisting of hydrogen, an amino acid, a dipeptide, a tripeptide, and a carbobenzoxy group;
B and E are selected from the group consisting of amino acid, a dipeptide, and a tripeptide;
C is cysteamine;
D is an amino acid or polypeptide comprising up to and including three amino acids; and
S is a sulfur atom in the cysteamine in C and in the amino acid or polypeptide in D.

3. The compound Cbz-(Beta)-Ala-Cystine-(Beta)-Ala-Cbz.

* * * * *